United States Patent [19]

Andrews et al.

[11] 4,336,796
[45] Jun. 29, 1982

[54] ADJUSTABLE LOWER EXTREMITY SPLINT WITH SINGLE POINT SUSPENSION

[76] Inventors: E. Trent Andrews, 2 Northgate Dr., San Francisco, Calif. 94127; Robert Moore, 4010 East Ave., Hayward, Calif. 94542

[21] Appl. No.: 174,567

[22] Filed: Aug. 4, 1980

[51] Int. Cl.³ .............................................. A61F 5/04
[52] U.S. Cl. ................................... 128/87 R; 128/88
[58] Field of Search ............... 128/83, 84 R, 85, 87 R, 128/88, 92

[56] References Cited

U.S. PATENT DOCUMENTS

| | | | |
|---|---|---|---|
| 3,417,748 | 12/1968 | Bimler | 128/85 |
| 3,651,803 | 3/1972 | Bimler | 128/88 |
| 3,762,405 | 10/1973 | DeGeorge | 128/88 |

Primary Examiner—John D. Yasko
Attorney, Agent, or Firm—Bielen & Peterson

[57] ABSTRACT

A lower extremity splint for use with a conventional traction apparatus to achieve a balanced single point suspension and traction of the lower extremity of a user, the lower extremity splint having a sling supported by a skeletal frame structure conforming to the outer periphery of the user's lower extremity, the frame structure being formed by two substantially parallel articulated primary members arrangeable on each side of the user's lower extremity, the primary members each having an articulation joint substantially centrally located, dividing each primary member into an upper thigh segment and a lower leg segment, the primary members being interconnected by a cross member between the distal end of the lower leg segment, a bridge member between the proximal end of the upper thigh segment and a bridge member between the articulation joint, wherein the splint is independently suspended from the traction apparatus.

9 Claims, 11 Drawing Figures

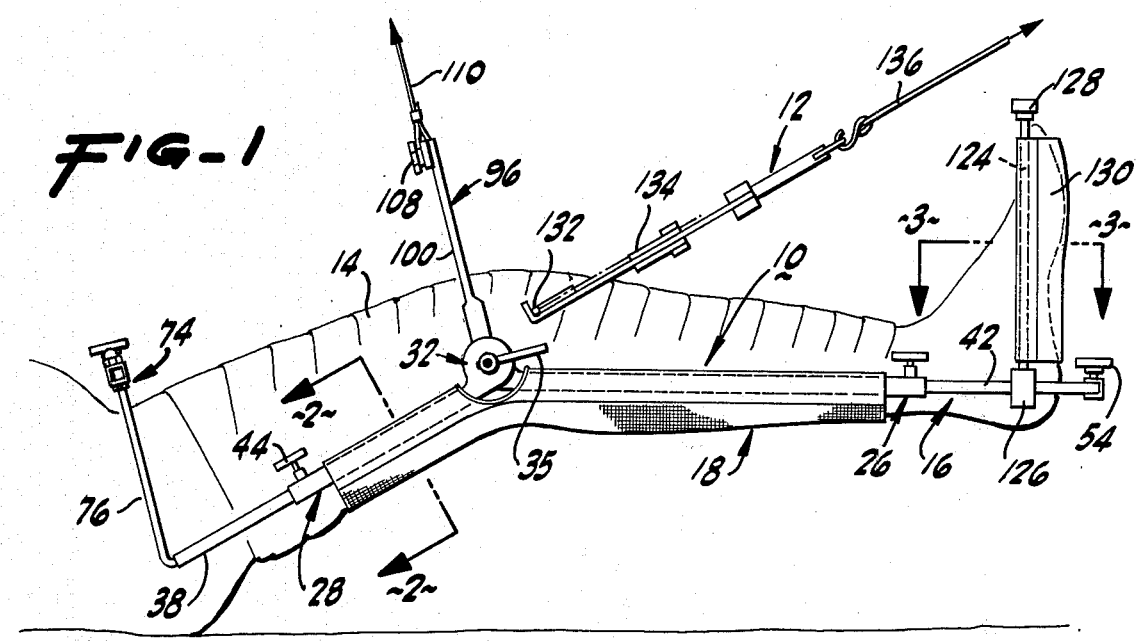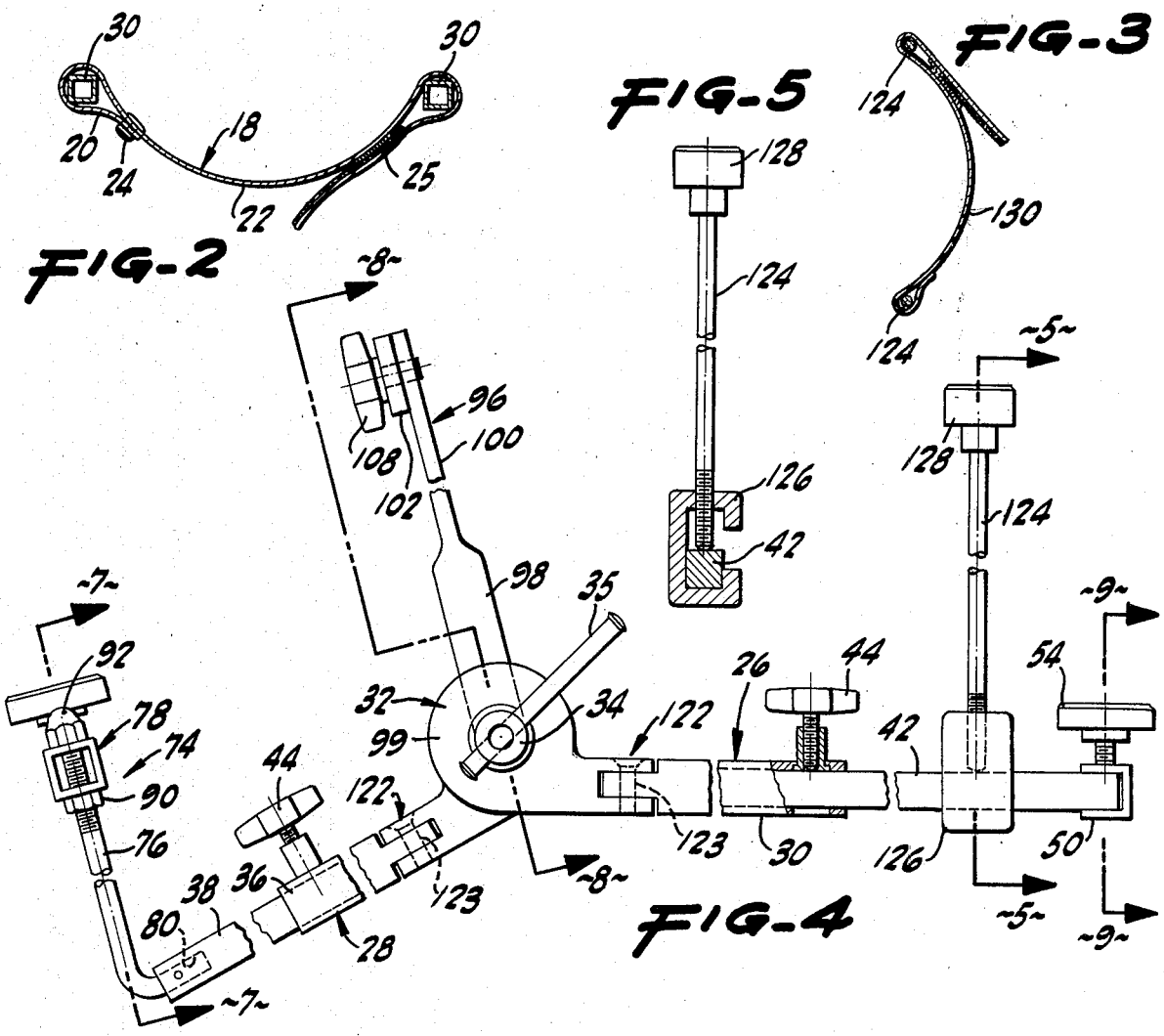

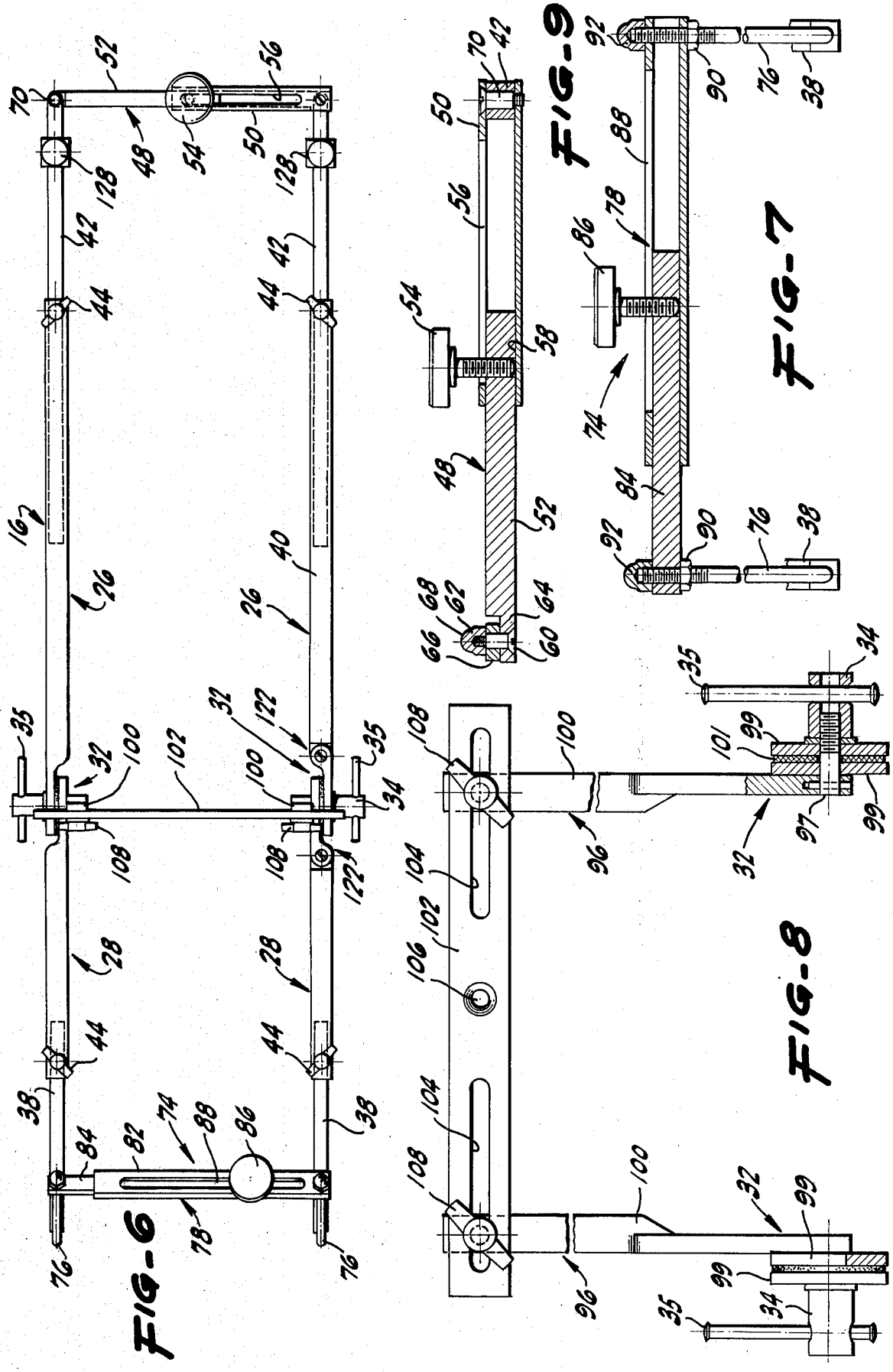

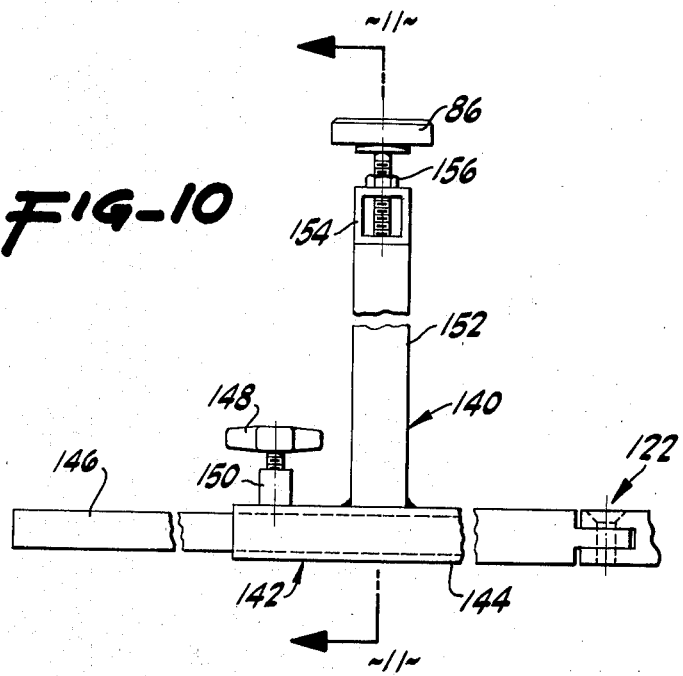
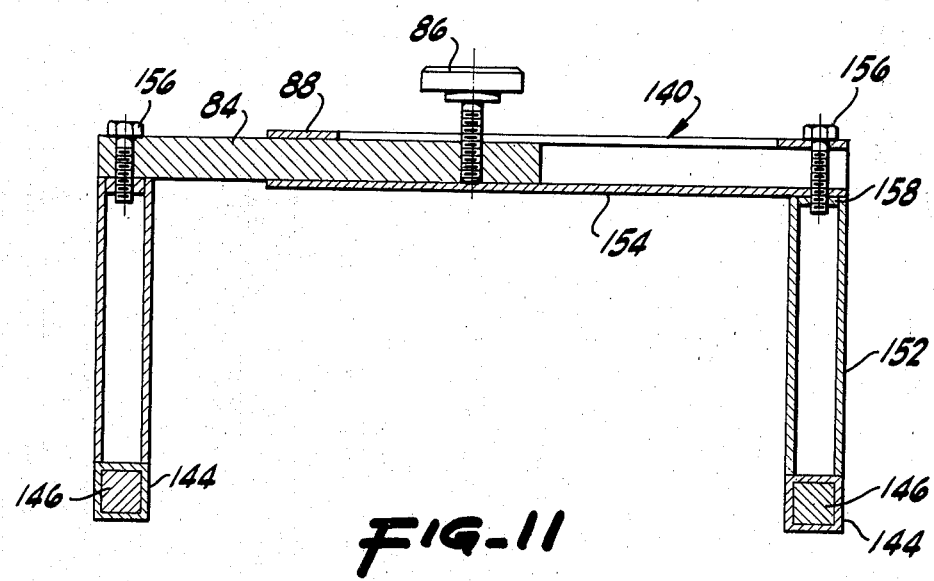

ADJUSTABLE LOWER EXTREMITY SPLINT WITH SINGLE POINT SUSPENSION

BACKGROUND OF THE INVENTION

This invention relates to a lower extremity splint which is particularly designed for hospital bed traction systems. The lower extremity splint is constructed for complete adjustment to the lower extremity of the patient and is designed for single point suspension from an overhead traction frame, or other means of suspension or support.

Splints have been commonly used to immobilize bone fractures. Splints may comprise simple rigid members, such as wooden slats lashed or taped in a parallel fashion to the fractured limb member for maintaining alignment and immobilization of the fractured member. While such simple devices are adequate for emergency first aid use in preventing further damage and in limiting discomfort, they are generally inadequate to maintain a proper set of the fracture for optimum healing.

A person's skeletal system is held in place and selectively moved by muscles and connective ligaments and tendons. All movement is effected by contraction of select muscles while opposing muscles, which enable a reverse movement on contraction, are relaxed. Because healthy skeletal muscles have a constant tone, or readiness which exists as a continued light state of contraction, there is exerted a slight longitudinal compressive force on the bone structure associated with the particular muscle or muscle group. When a break of the bone occurs the compressive force may cause misalignment or impacting or overlap of the fracture shortening the effective length of the bone. This deforming force is further enhanced by spastic contraction of muscle that has been traumatized.

To restore the bone to as close to original configuration as possible, the pull of the muscle groups must be overcome by an externally applied force which is accomplished by a device which applies a traction to the bone or bone structure. The traction device is constructed to apply a constant pulling force to overcome the compressing force of the muscles. This constant pulling force is best applied be weights and pulleys, which allows the bed confined patient a limited degree of movement while maintaining the constancy of the applied force.

When the fracture is in a limb member and requires traction for proper setting and knitting of the bone, a frame device for select orientation and support of the limb member is arranged on the patient for cooperation with a traction device mounted to the patient's bed.

The frame device is essentially an elaborate splint which for traction systems must be capable of properly orienting and positioning the fractured limb member for suspension and traction. The splint of the subject invention is designed for use on a patien's lower extremity and is improved over prior lower extremity splints by maximizing the adjustability and adaptability in order to conform to the particular shape of the user's lower extremity. This provides maximum comfort and minimum structure to the frame configuration of the splint. In minimizing the structure of the frame configuration, not only is the mobility and ease of handling and setting up the splint facilitated, but the close conformance with the user's lower extremity prevents inadvertent contact with projecting frame structures that would disturb the set of the fracture. The universal adjustability of the structure of the splint frame is arranged to allow readjustment for repositioning of the lower extremity during traction or articulation at the knee for exercise of the lower extremity. Further, the improved structural configuration of the invented splint allows a single point suspension from an overhead support eliminating the usual double point suspension of prior art conventional systems. The single point suspension of the lower extremity splint cooperates with the applied tension of the traction mechanism which is connected to the patient's lower extremity by a strap hitch or a bone pin to direct the tension forces for proper maintenance of alignment of the fractured bone.

SUMMARY OF THE INVENTION

The adjustable, lower extremity splint of this invention comprises a splint frame structure that is fully adjustable to closely conform the splint to the lower extremity of the injured user in the desired select position for cooperative use with a traction mechanism. Because the lower extremities of different injured persons are different in shape, length and other dimensional characteristics, a splint should be reasonably adaptable to a wide range of morphology. Further, because the nature and location of the injury may vary, the splint should be adjustable for properly positioning the lower extremity in the splint and properly orienting the splint and lower extremity with respect to the traction apparatus.

In accomplishing these objectives, the splint of this invention is constructed with a frame structure that is fully adjustable in length and width, and in angular articulation at a central pivot joint to allow the frame structure to closely conform to the peripheral contour of the user's lower extremity. The skeletal frame structure comprises two primary members which are substantially parallel and arrangeable on each side of a user's lower extremity. The primary members each have an articulation joint substantially centrally located on the primary members, dividing the primary members into a thigh segment and a lower leg segment. These segments are adjustable to correspond to the length of the user's thigh and leg with reference to the articulation joint which is positioned adjacent the user's knee. To maintain the desired spatial relationship of the two primary members, the frame structure includes a series of cross support structures. The distal ends of the leg segments are inerconnected by a cross member which is adjustable to vary the span between two primary members at the location where the user's feet are supported. For a similar function, the thigh segments are interconnected by an upper bridge member structurally resembling a construction bent which is adjustable to vary the span between the primary members at the location of the upper thigh. Similarly the central portion of the primary members at the articulation joints are interconnected by a central bridge member or structural bent which is adjustable to regulate the span between the primary members at the location of the user's knee. The bridge members are designed to allow the user's lower extremity to be positioned between the primary members of the frame and supported on a sling. The bridge members rise above the user's lower extremity and cross over the lower extremity to perform the structural task of interconnecting the primary members without interfering with the positioning of the lower extremity on the sling, which is arranged between and supported by primary frame members. The articulation joints are pivotally adjustable in a first angular plane to allow the lower extremity to be supported in a bent position if desired. At least one of the articulation joints may be concurrently adjustable in a second angular plane normal to the first plane to allow for regulation of the span between the joints independently of the span at either end of the frame structure. The bridge members comprise projecting elements on each opposed primary member and an interconnecting cross element.

The cross element of the central bridge member includes a connecting means for a single point connection of the splint to an overhead frame assembly of a traction apparatus. Independently, without necessarily contacting the splint structure, a traction cable in connected at some point to the user's lower extremity. The traction cable connects to a weight suspended over a pulley to exert a constant traction tension to the user's limb.

These and other features will become apparent from a detailed consideration of the preferred embodiment.

BRIEF DESCRIPTION OF THE DRAWINGS

FIG. 1 is a side elevational view of the lower extremity splint with installed sling for support of user's lower extremity associated traction apparatus.

FIG. 2 is a cross sectional view taken on the lines 2—2 in FIG. 1.

FIG. 3 is a cross sectional view taken on the lines 3—3 in FIG. 1.

FIG. 4 is an enlarged side elevational view, partially fragmented and partially in cross section of the lower extremity splint of FIG. 1.

FIG. 5 is an elevational cross sectional view taken on the lines 5—5 in FIG. 4.

FIG. 6 is a top view of the straightened lower extremity splint of FIG. 4.

FIG. 7 is a cross sectional view taken on the lines 7—7 in FIG. 4.

FIG. 8 is a cross sectional view taken on the lines 8—8 in FIG. 4.

FIG. 9 is an elevational cross sectional view taken on the lines 9—9 in FIG. 4.

FIG. 10 is a partial side elevational view of a modified portion of the splint.

FIG. 11 is a cross sectional view taken on the lines 11—11 in FIG. 10.

DETAILED DESCRIPTION OF THE PREFERRED EMBODIMENTS

Referring to the elevational schematic view of FIG. 1, the lower extremity splint 10 and associated traction apparatus 12 are shown with a patient's lower extremity 14 illustrated in the splint 10 and placed elevational support in traction by the traction apparatus 12. The lower extremity splint 10 comprises a frame structure 16 which supports a sling 18 in which the lower extremity is cradled. The sling 12 is fastened by overlapping flaps 20 connected to the body 22 of the sling by snaps 24, and by adjustable matte and hook fasteners 25, as shown in FIG. 2.

The frame structure 16 of the splint 10 comprises two substantially parallel primary, lateral members 26, shown in FIG. 6, which are arranged on each side of the injured lower extremity. The primary lateral members 26 are formed in two segments, a thigh segment 28 arranged on each side of the thigh, and a leg segment 30 arranged on each side of the leg. The two segments are interconnected at an articulatable joint 32, which allows the segments to be pivotal in an angular plane about a substantially horizontal axis. In this manner, a comfortable "bent" configuration can be achieved, as shown in FIG. 1. The degree of bend depends upon the preference of the attending physician and the nature of the injury. The selected configuration can be locked at the selected pivot angle by tightening a clamping boss 34 which screw tightens the joint 32. This same boss 34 can be loosened to allow the user to bend his lower extremity at his knee joint during suspension and traction allowing a limited degree of exercise to prevent stiffening of the knee joint and atrophy of the thigh muscles. During this procedure, the leg can be provided with a counter balance mechanism connected to the traction apparatus and leg. The boss 34 has a cross pin 35 for leverage in tightening when it is desired to secure the frame structure into a rigid structure.

The two segments 28 and 30 making up the primary lateral members of the splint, are themselves comprised of two adjustable elements. The thigh segment 28 is constructed with an elongated casement element 36 into which is telescoped an extension element 38 enabling the effective length of the thigh segment 28 to be shortened or elongated to accomodate the particular length of the thigh of the patient. Similarly, the leg segment 30 is constructed with an elongated casement element 40 into which is telescoped an extension element 42 enabling the effective length of the leg segment 30 to be shortened or elongated to accomodate the particular length of the leg of the patient. A threaded hand setscrew 44 is threaded through a boss 46 on the casement elements, as shown in greater detail in the exemplars of FIG. 4, to engage and lock the extension element with respect to the casement elements in the frame structure.

The primary lateral members 26 are maintained in position along the sides of the patient's lower extremity by a series of cross support structures. At the distal end of the leg segments 30 is an interconnecting cross member 48 comprising a casement element 50 in which is telescopically engaged an extension member 52 whereby the effective width of the frame structure 16 can be varied at the end proximate the user's feet. The extension member 52 is locked in desired position by a hand setscrew 54 passing through a slide slot 56 in the casement element 50 and threaded through the extension member to engage the inside wall 58 of the casement element 50, as shown in greater detail in FIG. 9.

To allow for adjustment of the cross member 48 with respect to the lateral members 26, the cross member 48 is pivotally connected to the ends of the lateral members by a pin 60 with a threaded end 62 passing through a coupling tongue 64 on the extension element 52 of the cross member and through a coupling tongue 66 on the extension element 42 of the leg segment 30 of one of the lateral members. The threaded end 62 engages a cap nut 68 to secure the pin and lock the frame in the desired position, as shown in FIG. 9.

The opposite end of the cross member 48 connects the casement element 50 to the extension element of the leg segement of the opposite lateral member by a pin 70 which passes through one side of the casement element and through the extension element 42 of the leg segment and threadably engages the opposite side of the casement element as shown in FIG. 9. A portion 72 of one side at the end of the casement element of the cross member is notched out to allow for insertion of the end of the extension element as shown.

The opposite end of the frame structure 16 of the splint 10 is interconnected by a bridge member 74 constructed in the form of a structural bent with risers 76 and a cross truss 78. The risers 76 are fabricated from rod stock and are inserted into sockets 80 in the ends of the extension elements 38 of the thigh segments 28. The risers are formed into a forward cant to allow for as much room and freedom to the user as possible.

The cross truss 78 comprises a casement element 82 into which is telescopically inserted an extension element 84. A hand setscrew 86 passes through an elongated slide slot 88 in the top side of the casement element 82 and is threaded through the extension element to engage the inside wall of the casement element in a manner identical to the hand setscrew 54 on the cross member at the foot of the frame structure, as shown in FIG. 7.

The use of a slot configuration as opposed to a simple hand setscrew and boss arrangement, as shown in FIG. 4, prevents the frame from inadvertently being pulled apart during opening as the setscrew engages the end of the slot preventing further movement.

The risers 76 are connected to the cross truss 78 by a stop nut 90 and cap nut 92 which bracket the casement element 82 on one side of the frame and the extension element 84 on the opposite side of the frame. This manner of connection allows a degree of pivot at the point of connection allowing, in the usual case, the lateral member on the outside of the patient's thigh to be extended to a substantially greater length than the lateral member on the inside of the patient's thigh, wherein a greater support is achieved. This adjustment can be made to either lateral member to allow the frame structure to be adapted to either lower extremity of the patient. The forward cant to the risers 76, as noted, allow greater freedom to the patient and permit the patient to sit. The risers or any frame element can be covered with a protective covering such as foam or other cushioning material for comfort.

A somewhat similar bridge member 96 allows for structural stability and adjustment at the joint 32 of the frame structure. This bridge member 96 is connected to the opposed joints 32 by a strut member 98 which is journal connected to the joint and secured to the clamping boss 34. The clamping boss is threaded to a journal shaft 97 pinned to the strut. The frame structure joints include flange plates 99 between which is sandwiched a leather friction disc 101, the plates 99 being freely pivotable on the journal shaft 97 until clamped by the clamping boss 34, as shown in FIG. 8.

The strut members 98 support a riser bar 100 connected to a cross bar 102. The cross bar 102 has two slots 104 on each side of a central support hole 106 allowing for adjustment of the span between the lateral primary members 26 and select off center positioning of the center support hole 106. The selected positioning if fixed by tightening clamping screws 108 which pass through the cross bar 102 and threadably engage the riser bars 100.

The entire frame structure 16 of the splint 10 and cradled lower extremity is supported at the support hole 106. A cable 110, shown in FIG. 1, connects the frame structure of the splint to a conventional overhead support device for the cable (not shown). The single point suspension allows the frame structure and lower extremity to be tilted inward or outward to improve the positioning of the lower extremity with regard to the nature and location of the injury. This is accomplished by off centering the support hole on the cross bar.

Because the span of the frame structure can be adjusted substantially at the center without regard to the span adjustment at the ends of the structure, at least one of the lateral members has an articulation about a substantially vertical axis, i.e. on normal to the formerly described articulation. This is accomplished by a tongue and fork interconnection 122 of the casement elements 36 with the frame structure joints 32 allowing select adjustment of any one of the thigh or shin segments. Adjustment can be made and fixed by use of a tightening screw 123 shown in FIG. 4. This additional feature to the basic unit allows maximum independent adjustment of the various components.

As an optional component, the frame structure can be fitted with web support rods 124 which connect to the extension element 42 on the leg segments 30 by a clamping bracket 126 in which the threaded end of the support rods 124 function as setscrews to engage the surface of the extension element. The support rods have a protective end cap 128 and support an elastic web 130 with matte and hook fasteners 131 which spans the two rods and functions as a foot support to maintain an upright positioning of the foot for prevention of muscle atrophy, as shown in FIG. 3. The elasticity of the web allows active resistive foot exercises to be performed by the patient.

As an alternate embodiment to the bridge member 74 shown in FIG. 4 and in FIG. 7, the bridge member 140 of FIGS. 10 and 11 provides a somewhat more rigid construction. Referring to FIGS. 10 and 11, thigh segments 142 are shown with casement elements 144 into which are telescoped extension elements 146. The extension elements are adjustable and fixed in position by tightening of a hand setscrew 148 threaded through a boss 150 at the end of each of the casement elements 144.

Proximate the end of each of the casement elements 144 is a rigid riser 152 which is welded to the top of each of the casement elements to form a part of the bridge member 140. Interconnecting the projecting ends of the two risers is a cross truss 154 which is constructed similarly to the cross truss 78 of the prior embodiment. The cross truss 154 is connected to each riser 152 by a bolt 156 passing through the ends of the cross truss 154 and engaged with a threaded end plug 158 in the risers, allowing the degree of limited pivot described in connection with the first embodiment. The alternate embodiment is less confining at the upper thigh, yet provides substantially the same degree of rigidity to the frame structure when fixed in position as the previously described embodiment of the bridge member 74.

When used as a traction splint, the frame structure and cradled lower extremity are aerially supported as shown in FIG. 1. The lower extremity is placed in traction, for example, by a bone pin 132 and yoke 134 which is connected to a cable 136 to which is applied a tension. Minimum reduction is achieved by the single point suspension of the frame structure allowing accurate adjustment of the traction with respect to the fracture as required by the physician.

When not in use the frame structure can be folded into a substantially collapsed condition for compact storage.

While in the foregoing specification embodiments of the present invention have been set forth in considerable detail for the purposes of making a complete disclosure of the invention, it should be apparent to those of ordinary skill in the art that numerous changes may be made in such details without departing from the spirit and principles of the invention.

What is claimed is:

1. A lower extremity splint useable with an overhead suspension structure, said lower extremity splint comprising:

a frame structure having opposed first sides formed of lateral members, opposed second sides formed of cross structures connected to said lateral members, said lateral members each having a substantially centrally located articulation joint with locking means for select articulation and locked angular positioning of said lateral members on an axis common to said articulation joints, and a single support means connected to said frame structure proximate said articulation joints for supporting said frame structure from a single support line connected to the overhead suspension structure; and, sling means connected to said frame structure adapted for supporting a user's lower extremity in said splint.

2. The lower extremity splint of claim 1 wherein said support means comprises a bridge structure with opposed projecting elements connected to said frame structure and a cross element interconnecting said projecting elements, said cross elements having a connection means for connecting said cross element and connected frame structure to said suspension structure.

3. The lower extremity splint of claim 2 wherein said connection means comprises a support structure constructed to support said frame structure at one of a plurality of selectable points between said projecting elements.

4. The lower extremity splint of claim 3 wherein said support structure comprises a support device on said cross element in combination with adjustment means on said cross element for adjusting the position of said cross element with respect to said projecting elements.

5. The lower extremity splint of claim 1 wherein said lateral members each have:

a thigh segment with a joint connection end, a proximal end and means for adjusting the length of said thigh segments;

a leg segment with a joint connection end, a distal end and means for adjusting the length of said leg segment; and interconnection means connecting said thigh segment and said leg segment at said connection ends for pivotal displacement of said thigh segment with relation to said leg segment at said articulation joint.

6. The lower extremity splint of claim 5 wherein said cross structures comprises a cross member with means for adjusting the length of the cross member, said cross member having ends connected to the distal ends of said leg segments, and, a bridge structure having projecting elements and having a cross truss with opposed ends and means for adjusting the length of said cross truss, said projecting elements having first ends connected to the proximal ends of said thigh segments and second ends connected to the ends of said cross truss.

7. The lower extremity splint of claim 6 wherein said adjustment means of said thigh segments, said leg segments, said cross member and said cross truss comprise telescoping first and second elements and locking means for locking said first and second telescoped elements at a selected overall length.

8. The lower extremity splint of claim 1 having further at least one pivot joint at said articulation joint for pivotal articulation of at least one lateral member in a manner allowing independent adjustment of the span between said lateral members at said articulation joints.

9. The lower extremity splint of claim 1 wherein said lateral members have length adjustment means for variably adjusting the length of said lateral members and said cross structures have width adjustment means for adjusting the width of said cross structures, wherein said length and width adjustment means include locking means for adapting and rigidly conforming said frame structure to the periphery of a particular user's lower extremity for improving orientation on single point suspension.

* * * * *